United States Patent
Mizutani et al.

(10) Patent No.: US 7,087,151 B2
(45) Date of Patent: Aug. 8, 2006

(54) HYDROGEN SENSOR FOR USE IN BATTERY OVERCHARGE/OVERDISCHARGE DETECTOR AND HYDROGEN LEAKAGE DETECTOR

(75) Inventors: Keigo Mizutani, Okazaki (JP); Kazuhiko Yoshida, Takahama (JP); Hidetaka Hayashi, Nagoya (JP); Masayoshi Iwase, Anjo (JP); Kazuo Tojima, Toyota (JP)

(73) Assignees: Denso Corporation, Kariya (JP); Nippon Soken, Inc., Nishio (JP); Toyota Jidosha Kabushiki Kaisha, Aichi-ken (JP)

( * ) Notice: Subject to any disclaimer, the term of this patent is extended or adjusted under 35 U.S.C. 154(b) by 494 days.

(21) Appl. No.: 10/361,023

(22) Filed: Feb. 10, 2003

(65) Prior Publication Data

US 2003/0168337 A1 Sep. 11, 2003

Related U.S. Application Data

(62) Division of application No. 09/570,533, filed on May 12, 2000, now abandoned.

(30) Foreign Application Priority Data

May 13, 1999 (JP) .................... 11-132981
Apr. 14, 2000 (JP) .................... 2000-112976

(51) Int. Cl.
*G01N 27/407* (2006.01)
*G01N 27/41* (2006.01)

(52) U.S. Cl. .................... 205/783.5; 204/429
(58) Field of Classification Search .......... 205/783.5, 205/784, 784.5; 204/425, 426, 429; 73/23.31, 73/23.32

See application file for complete search history.

(56) References Cited

U.S. PATENT DOCUMENTS

| 3,325,378 A | 6/1967 | Greene et al. |
| 3,509,034 A | 4/1970 | Paine |
| 3,649,473 A | 3/1972 | Holden et al. |
| 3,928,161 A | 12/1975 | McIntyre et al. |
| 4,024,036 A | 5/1977 | Nakamura et al. |
| 4,040,930 A | 8/1977 | Dillon |
| 4,177,112 A | 12/1979 | Suzuki et al. |

(Continued)

FOREIGN PATENT DOCUMENTS

DE  38 76 013 T2  5/1988

(Continued)

OTHER PUBLICATIONS

Lu et al, Sensors and Actuators B 35-36, 1996, pp. 130-135.*

(Continued)

*Primary Examiner*—Kaj K. Olsen
(74) *Attorney, Agent, or Firm*—Nixon & Vanderhye, PC (57) ABSTRACT

A hydrogen sensor which may be employed in an overcharge/overdischarge detector for a battery and a hydrogen leakage detector for a fuel cell is provided. The hydrogen sensor includes a sensor element and a diffused resistor member. The gas to be measured passes through the diffused resistor member and reaches the sensor element. The sensor element outputs a signal indicative of the concentration of hydrogen contained in the gas as a function of a decrease in concentration of oxygen contained in the gas arising from reaction of the hydrogen on the oxygen. The diffused resistor member is so designed that speeds of diffusion of the hydrogen and the oxygen when passing through the diffused resistor member are different from each other for increasing the sensitivity of measurement of the concentration of hydrogen.

9 Claims, 6 Drawing Sheets

U.S. PATENT DOCUMENTS

| | | | |
|---|---|---|---|
| 4,190,499 A | 2/1980 | Pebler | |
| 4,560,444 A | 12/1985 | Polak et al. | |
| 5,676,811 A | 10/1997 | Makino et al. | |
| 5,879,526 A | 3/1999 | Dietz et al. | |
| 6,254,750 B1 * | 7/2001 | Patrick et al. | 204/425 |

FOREIGN PATENT DOCUMENTS

| | | |
|---|---|---|
| DE | 690 18 773 T2 | 11/1990 |
| DE | 691 13 866 T2 | 7/1991 |
| DE | 40 21 929 C2 | 1/1992 |
| DE | 195 32 158 A1 | 3/1996 |
| EP | 0267765 A2 | 5/1988 |
| EP | 0408039 A2 | 7/1990 |
| EP | 0294085 B1 | 11/1992 |
| EP | 0428130 B1 | 4/1995 |
| EP | 0668503 A1 | 8/1995 |
| EP | 0466067 B1 | 10/1995 |
| JP | 57048648 A | 3/1982 |
| JP | 03-051753 | 3/1991 |
| JP | 6-60884 | 8/1994 |
| JP | 08-122297 | 5/1996 |
| JP | 8-264208 | 10/1996 |
| JP | 10-50281 | 2/1998 |
| JP | 2000-009685 | 1/2000 |
| JP | 2000-065783 | 3/2000 |
| JP | 2000-253589 | 9/2000 |
| JP | 2000-258389 | 9/2000 |

OTHER PUBLICATIONS

Logothetis et al, High-Temperature Oxygen Sensors Based on Electrochemical Oxygen Pumping, pp. 136-154, from ACS Symposium Series 309, 1986.*

Grimsehl: Lehrbuch der Physik, Mechanik Warmelehre Akustik, Textbook for Physics: Mechanics Thermodynamics Acoustics, B. G. Teubner 1954, p. 406.

German Search/Examination Report and translation.

Notification of Reasons for Rejection—Japanese Application No. 2000-112976, dated Dec. 27, 2004.

* cited by examiner

HYDROGEN SENSOR FOR USE IN BATTERY OVERCHARGE/OVERDISCHARGE DETECTOR AND HYDROGEN LEAKAGE DETECTOR

This application is a divisional of application Ser. No. 09/570,533 filed May 12, 2000, now abandoned.

BACKGROUND OF THE INVENTION

1 Technical Field of the Invention

The present invention relates generally to a hydrogen sensor measuring the concentration of hydrogen contained in gasses, an overcharge/overdischarge detector and a hydrogen leakage detecting apparatus using a hydrogen sensor.

2 Background Art

Charge/discharge control systems are known which are designed to avoid overcharging and overdischarging of a storage battery mounted in electric vehicles or hybrid vehicles. Usually, the overcharging or overdischarging of a battery will cause combustible hydrogen to be generated within a battery chamber. It is, thus, necessary to inhibit the overcharging and overdischarging of the battery for safety purposes. The systems are designed based on the fact that a battery temperature rises during the overcharging and have temperature sensors measuring such a temperature rise of the battery. The overdischarging is detected based on the fact that the overdischarging will cause the voltage of the battery to be decreased.

It is also necessary for fuel cells using hydrogen to stop an operation of a hydrogen feed system feeding the hydrogen to a fuel electrode of the fuel cells if leakage of hydrogen occurs.

However, the above systems require installation of temperature sensors one for each cell of the battery. An increase in battery will, thus, result in a great increase in temperature sensor. During overdischarging, the temperature of the battery does not rise. The temperature sensors are used only in detecting the overcharging. Other means is, thus, needed for detecting the overcharging, thereby resulting in complex of the system.

The fuel cells are desired to detect the hydrogen leakage using a high sensitive yet simple structure.

SUMMARY OF THE INVENTION

It is therefore a principal object of the present invention to avoid the disadvantages of the prior art.

It is another object of the present invention to provide a hydrogen sensor designed to measure the concentration of hydrogen generated by overcharging and overdischarging of a battery with high accuracy.

It is a further object of the invention to provide an overcharge/overdischarge detector using a hydrogen sensor capable of measuring the concentration of hydrogen with high accuracy.

It is a still further object of the invention to provide a hydrogen leakage detector designed to detect a leakage of hydrogen from a hydrogen supply system for a fuel cell.

According to one aspect of the invention, there is provided a hydrogen sensor. The hydrogen sensor comprises: (a) a sensor element outputting a signal indicative of a concentration of hydrogen contained in a gas as a function of a decrease in concentration of oxygen contained in the gas arising from reaction of the hydrogen on the oxygen; and (b) a diffused resistor member through which the gas is introduced to the sensor element, the diffused resistor member being so designed that speeds of diffusion of the hydrogen and the oxygen when passing through the diffused resistor member are different from each other.

In the preferred mode of the invention, the sensor element has a limiting current producing structure which includes a pair of electrodes formed on surfaces of a base made of an oxygen ion-conductive solid electrolyte. One of the electrodes is exposed to the gas through the diffused resistor.

The diffused resistor member is formed by one of a porous material and a member having formed therein a pin hole.

The base has a test tube-like shape. The electrodes are disposed on opposed portions of inner and outer surfaces of a tip portion of the base.

The base may alternatively have a plate-like shape. The electrodes may be disposed on opposed surfaces of the base.

The base may be formed by a laminate of plate members which forms therein a gas chamber into which the gas is introduced. One of the electrode is exposed to the gas chamber.

The pin hole is formed in the laminate to establish communication between the gas chamber and an outer surface of the laminate on which the other electrode is formed.

A porous protective layer may further be formed on the outer surface of the laminate to cover the electrode formed on the outer surface of the laminate and the pin hole.

According to the second aspect of the invention, there is provided an overcharge/overdischarge detecting apparatus for a battery which comprises: a hydrogen sensor and an overcharge/overdischarge detecting circuit. The hydrogen sensor includes, (a) a sensor element outputting a signal indicative of a concentration of hydrogen contained in a gas generated within a battery as a function of a decrease in concentration of oxygen contained in the gas arising from reaction of the hydrogen on the oxygen, and (b) a diffused resistor member through which the gas is introduced to the sensor element, the diffused resistor member being so designed that speeds of diffusion of the hydrogen and the oxygen when passing through the diffused resistor member are different from each other. The overcharge/overdischarge detecting circuit receives the signal outputted from the sensor element of the hydrogen sensor to monitor the concentration of hydrogen to determine whether the battery is in one of overcharged and overdischarged state or not.

According to the third aspect of the invention, there is provided a hydrogen leakage detecting apparatus for a hydrogen supply system supplying hydrogen to a fuel cell which comprises a hydrogen sensor and a hydrogen leakage determining circuit. The hydrogen sensor disposed near the hydrogen supply system, the hydrogen sensor including, (a) a sensor element outputting a signal indicative of a concentration of hydrogen contained in a gas existing near the hydrogen supply system as a function of a decrease in concentration of oxygen contained in the gas arising from reaction of the hydrogen on the oxygen, and (b) a diffused resistor member through which the gas is introduced to the sensor element, the diffused resistor member being so designed that speeds of diffusion of the hydrogen and the oxygen when passing through the diffused resistor member are different from each other. The hydrogen leakage determining circuit receives the signal from the hydrogen sensor to determine whether the hydrogen leaks from the hydrogen supply system or not.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
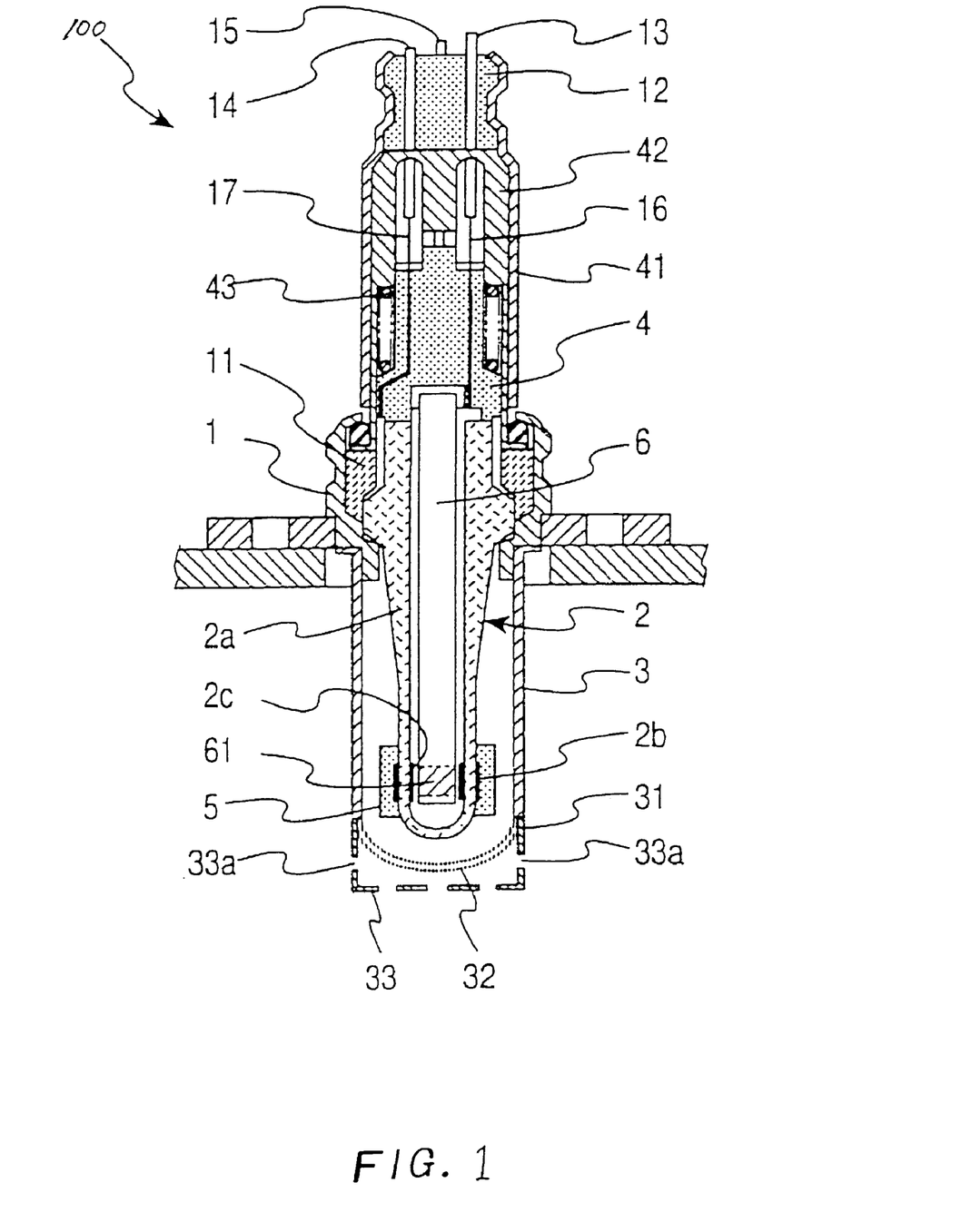
FIG. 1 is a longitudinal sectional view which shows a hydrogen sensor according to the first embodiment of the invention.

Referring now to the drawings, wherein like numbers refer to like parts in several views, particularly to FIG. 1, there is shown a hydrogen sensor 100 according to the first embodiment of the invention.

The hydrogen sensor 100 generally includes a cylindrical housing 1, a cylindrical cover 3, and a sensing element 2. The housing 1 has a mount flange disposed on the periphery thereof. The cover 3 is connected at one end thereof to the housing 1. The sensing element 2 is installed within the cover 3. The housing 1 and the cover 3 are both made of material such as a stainless steel resistance to a hydrogen gas to be measured.

The sensing element 2 consists of an upper half retained within the housing 1 through an insulator 11 and a lower half projecting from the housing 1 into the cover 3. The cover 3 has an opening 31 formed in the bottom thereof which serves as a gas inlet. The gas inlet 31 is covered with a semi-circular explosion-proof wire gauze 32 for avoiding the flame propagation. Usually, when a flammable gas such as hydrogen gas are measured, the concentration of hydrogen contained in the gas may fall within an explosive range, resulting in firing. If such a condition is encountered, the wire gauze 32 absorbs the heat of the fire to avoid expansion of the fire. For avoiding breakage of the wire gauze 32, a cup-shaped protector 33 is installed over the wire gauze 32. The protector 33 has a plurality of through holes 33a for passage of the gas to be measured. The wire gauze 32 consists of an outer and an inner net which are overlaid with a given gap therebetween and whose hole size is determined so as to avoid the expansion of flame effectively.

A ceramic cover 4 is disposed on an end of the sensing element 2 so as to close an upper end opening of the housing 1. Specifically, the ceramic cover 4 is fixed at a lower end thereof within the upper end opening of the housing 1. A hollow cylindrical metallic cover 41 is installed above the housing 1 to surround an upper peripheral portion of the cover 4. The cover 41 has an upper end opening closed by an insulator 12. A ceramic hollow cylinder 42 is fitted within the cover 41 beneath the insulator 12. Between an inner shoulder portion of the cylinder 42 and an outer shoulder portion of the cover 4, a coil spring 43 is disposed to urge the cover 4 downward into constant engagement with the sensor element 2.

The sensor element 2 consists of a test tube-like base 2a made of an oxygen ion-conductive solid electrolyte such as zirconia, outer and inner electrodes 2b and 2c made of platinum, and a diffused resistor layer 5. The outer and inner electrodes 2b and 2c are attached to outer and inner wall of an end portion of the base 2a so as to face each other. The diffused resistor layer 5 covers the outer electrode 2b completely and is made of a porous alumina for allowing the gas to reach the outer electrode 2b therethrough.

The base 2a has disposed within a chamber thereof a heater 6 which includes a heat generating portion 61 facing the inner electrode 2c. The electrodes 2b and 2c are connected to leads 16 and 17 through conductors (not shown) formed on an outer surface of the base 2a. The leads 16 and 17 are connected to terminals 13 and 14 retained within the insulator 12. The heater 6 is connected to a terminal 15 retained in the insulator 12. The chamber of the base 2b communicates with the atmosphere through air vents (not shown) formed in the cover 41 and fine passage formed between the parts.

Figure 2:
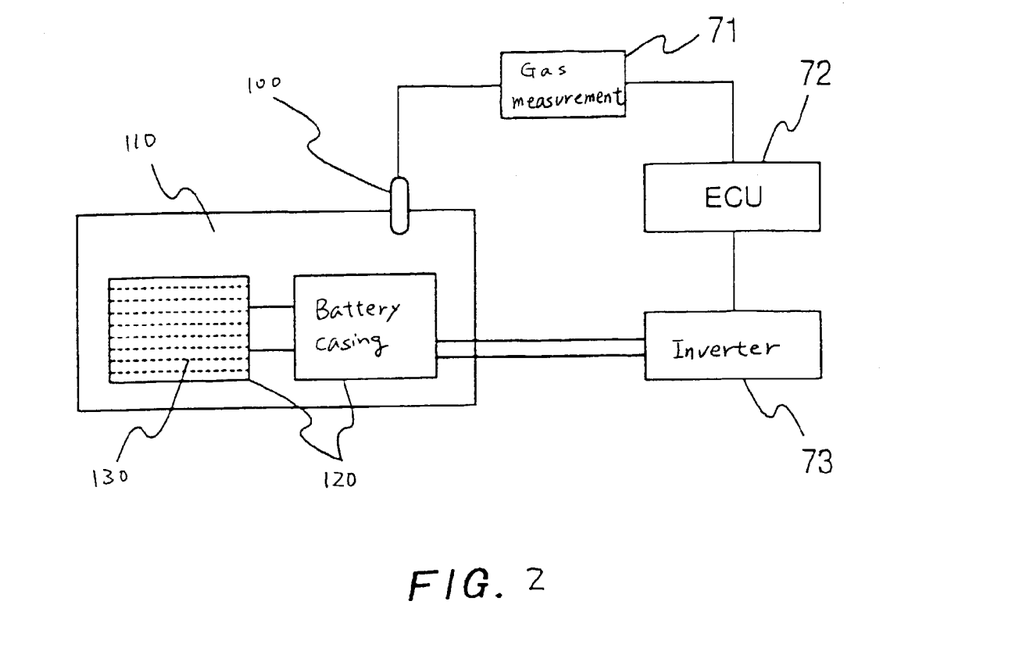
FIG. 2 is a block diagram which shows a charge/discharge control system using the hydrogen sensor in FIG. 1.

FIG. 2 shows an example in which the hydrogen sensor 100 is used with a charge/discharge control system mounted in a hybrid vehicle or an electric vehicle. The charge/discharge control system includes a gas measurement circuit 71, an electronic control unit (ECU) 72, and an inverter 73. The hydrogen sensor 100 is installed in an upper wall of a chamber 110 of a storage battery. In the chamber 110, battery casings 120 are disposed each of which has a plurality of nickel hydrogen cells 130 whose output current is supplied to the inverter 73 and converted into an alternate current.. The hydrogen sensor 100 is connected to the ECU 72 through the gas measurement circuit 71. The ECU 72 uses the concentration of hydrogen contained in a gas measured by the hydrogen sensor 100 to determine the overcharging or overdischarging of the storage battery for controlling charging/discharging operations thereof.

The gas generated in the battery chamber 110 is introduced inside the cover 3 of the hydrogen sensor 100 through the through holes 33a of the protector 33 and the wire gauze 32 and reaches the electrode 2b of the sensor element 2 through the diffused resistor layer 5. Application of dc voltage to the electrodes 2b and 2c attached to the base 2a where the electrode 2c is connected to a positive (+) point of a voltage source will cause oxygen contained in the gas reaching the electrode 2b to be ionized and moved to the electrode 2c through the electrode 2b, thereby resulting in flow of a limiting current through the electrodes 2b and 2c as a function of the concentration of oxygen in the gas. When the hydrogen is produced in the battery chamber 110 due to the overcharging or overdischarging of the storage battery, it reacts on the oxygen, thereby resulting in a decrease in output from the electrodes 2*b* and 2*c*. Specifically, the limiting current flows through the electrodes 2*b* and 2*c* as a function of a change in concentration of oxygen arising from a change in concentration of hydrogen. The concentration of hydrogen may, thus, be determined by measuring the limiting current.

Figure 6:
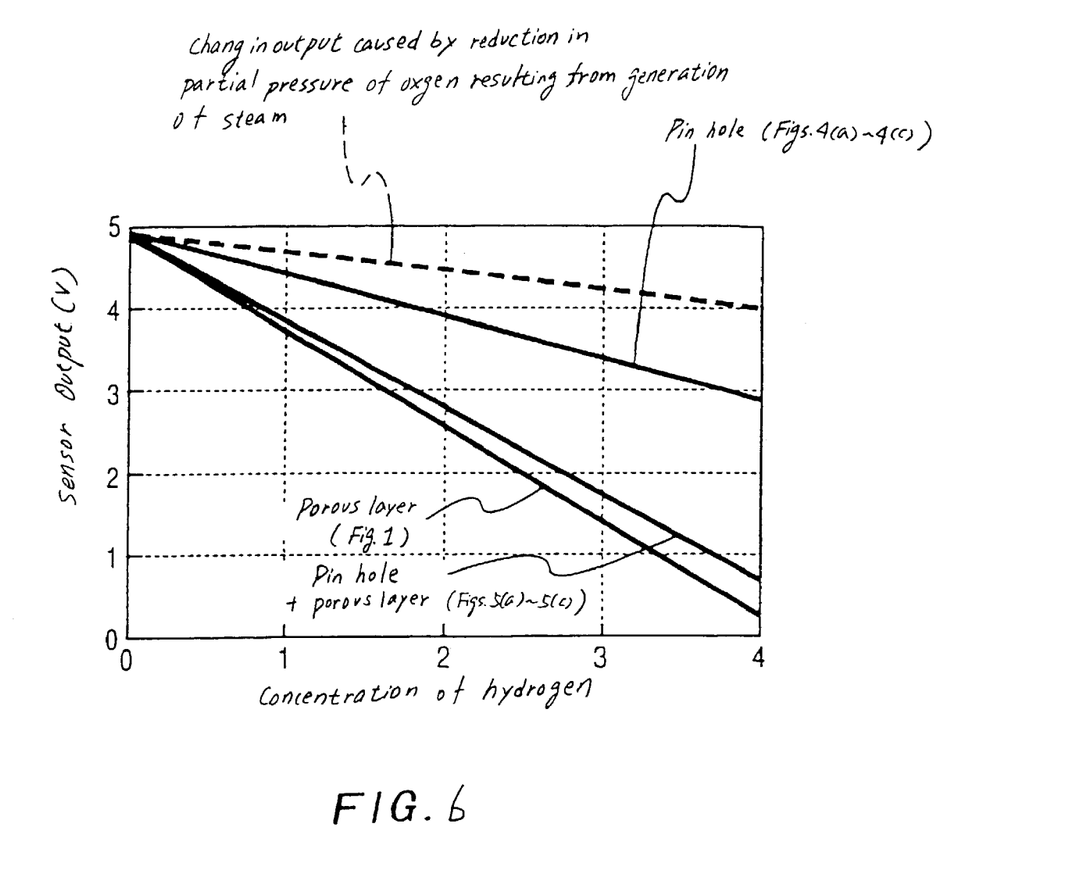
FIG. 6 is a graph which shows a relation between a sensor output and the concentration of hydrogen contained in a gas to be measured.

Usually, when a battery is overcharged or overdischarged, it will cause the hydrogen and oxygen of 2:1 to be generated. Thus, when the hydrogen and oxygen are burnt completely, it results in only a change in concentration of oxygen, as indicated by a broken line in FIG. 6, equivalent to a decrease in partial pressure of the oxygen caused by steam generated by the burning. However, the diffused resistor layer 5 used in the hydrogen sensor 100 of this embodiment passes the hydrogen therethrough faster than the oxygen, thereby causing the concentration of oxygen to be decreased on the electrode 2*b*, as indicated by the lowermost solid line in FIG. 6, more than that caused by the steam. The determination of concentration of hydrogen may, thus, be achieved with high accuracy by measuring the decrease in concentration of oxygen. Specifically, the overcharging and overdischarging of the storage battery may be detected by measuring the decrease in concentration of oxygen. FIG. 6 shows a change in sensor output as a function of concentration of hydrogen when the hydrogen and oxygen of 2:1 are generated in case of the overcharging and overdischarging. The rates or speeds of diffusion of hydrogen and oxygen when passing through the diffused resistor layer 5 depend upon the porosity of the diffused resistor layer 5. The difference in speed of diffusion between the hydrogen and the oxygen may, thus, be increased to a desired value by setting the porosity of the diffused resistor layer 5 properly. In this embodiment, the diffused resistor layer 5 is designed to have a porosity of 2 to 10% and a thickness of 200 to 1000 μm.

Figure 3:
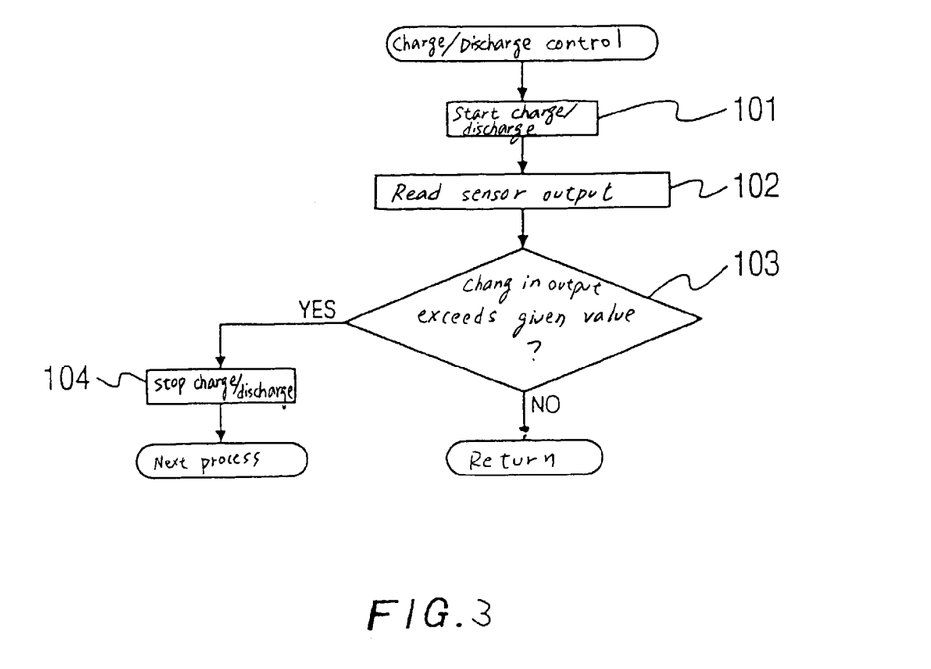
FIG. 3 is a flowchart of a program performed to detect overcharging and overdischarging of a battery.

FIG. 3 shows a flowchart of a program performed by the ECU 72 to control the charging and discharging of the storage battery.

After entering the program, the routine proceeds to step 101 wherein a charging or discharging operation is performed to charge or discharge the storage battery. The routine proceeds to step 102 wherein an output of the hydrogen sensor 100 is read. The routine proceeds to step 103 wherein it is determined whether a change in output of the hydrogen sensor 100 exceeds a given value or not. If the change exceeds the given value meaning that the hydrogen is being generated within the battery chamber 110, that is, that the storage battery is in an overcharged or an overdischarged state, then the routine proceeds to step 104 wherein the charging or discharging operation is stopped in the inverter 73. The routine proceeds to a given subsequent operation. If a NO answer is obtained in step 103, then the routine returns back to step 101 to allow the charging or discharging operation to continue.

Figure 4A:
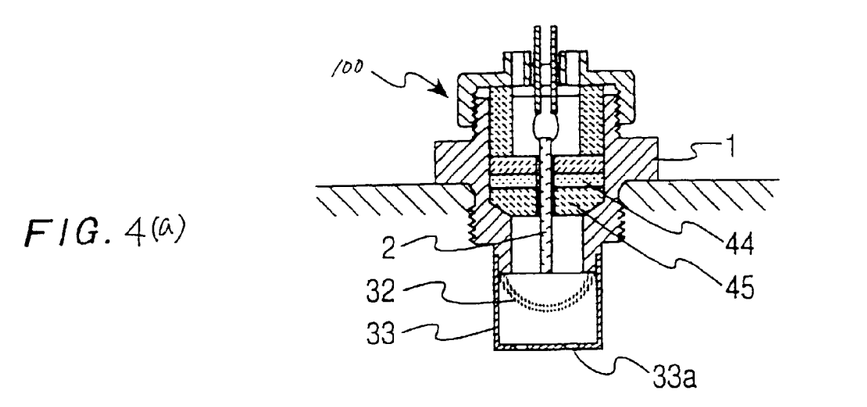
FIG. 4(a) is a cross sectional view which shows a hydrogen sensor according to the second embodiment of the invention.
Figure 4B:
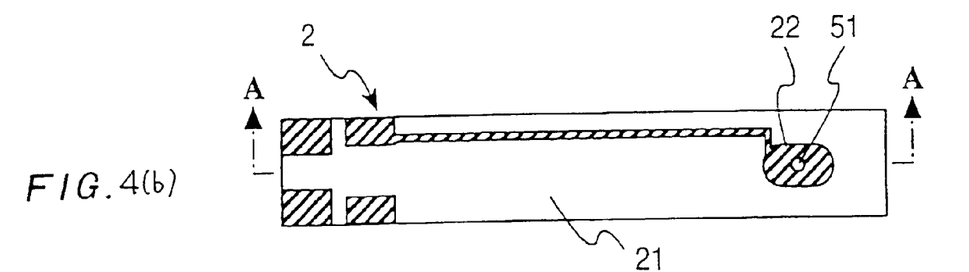
FIG. 4(b) is a plan view which show a sensor element of the hydrogen sensor shown in FIG. 4(a)
Figure 4C:
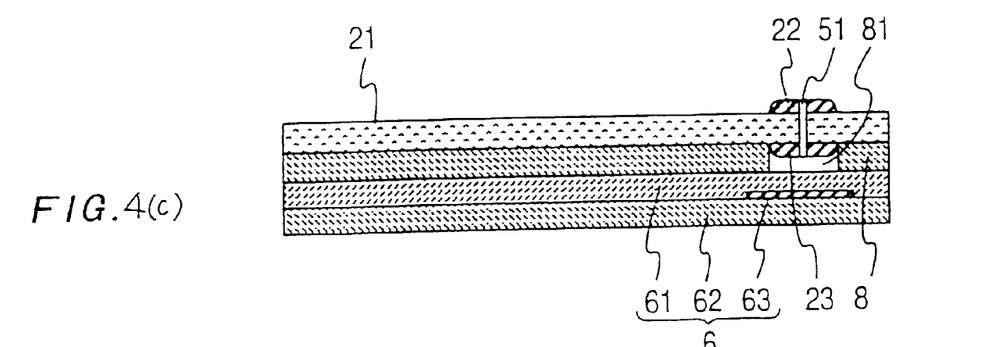
FIG. 4(c) is a cross sectional view taken along the line A—A in FIG. 4(b)

FIGS. 4(*a*), 4(*b*), and 4(*c*) show the hydrogen sensor 100 according to the second embodiment of the invention.

The hydrogen sensor 100 has a laminated sensor element made of zirconia sheets. The cylindrical housing 1 has, as clearly shown in FIG. 4(*a*), the sensor element 2 disposed therein through an insulator 45 and a gas sealing member 44. The explosion-proof wire gauze 32 and the protector 33 are, like the first embodiment, installed on the bottom of the housing 1. The sensor element 2 includes, as shown in FIGS. 4(*b*) and 4(*c*), a zirconia base 21 and electrodes 22 and 23 disposed diametrically on upper and lower surfaces of the zirconia base 21. The upper electrode 22 is exposed to a chamber in the housing 1. The lower electrode 23 is exposed to a chamber 81 formed in a spacer 8 disposed beneath the zirconia base 21. A heater 6 is disposed below the spacer 8 which is made of a laminate of alumina bases 61 and 62 and a platinum electrode 63 embedded between the bases 61 and 62.

A pin hole 51 is formed in the zirconia base 21 and the centers of the electrodes 22 and 23 to establish communication between the chamber 81 and the chamber in the housing 1 so that the gas in the housing 1 can enter the chamber 81. The size of the pin hole 51 is so determined as to set the speed of diffusion of the gas introduced into the chamber 81 to a desired value.

The operation of the hydrogen sensor 100 of this embodiment is substantially the same as that in the first embodiment. Specifically, application of dc voltage to the electrodes 22 and 23 where the electrode 22 is connected to a positive (+) point of a voltage source will cause a limiting current to flow through the electrodes 22 and 23 as a function of the concentration of oxygen contained in the gas entering the chamber 81 through the pin hole 51. The determination of the concentration of hydrogen is achieved by measuring a decrease in limiting current. A change in sensor output is indicated by the uppermost solid line in FIG. 6.

Figure 5A:
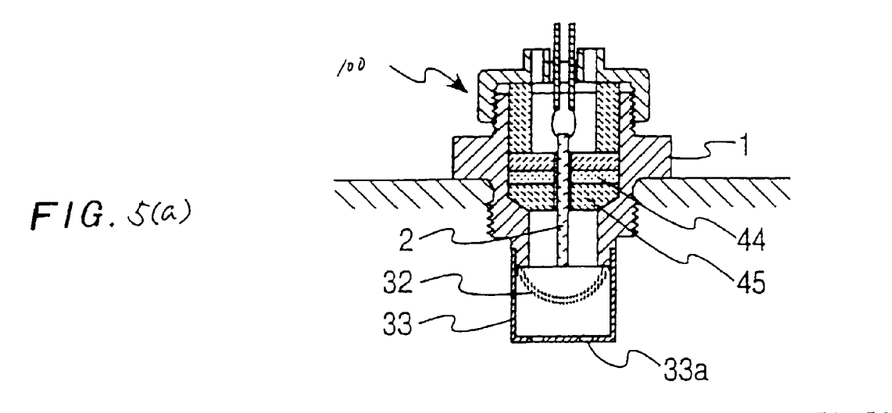
FIG. 5(a) is a cross sectional view which shows a hydrogen sensor according to the third embodiment of the invention.
Figure 5B:
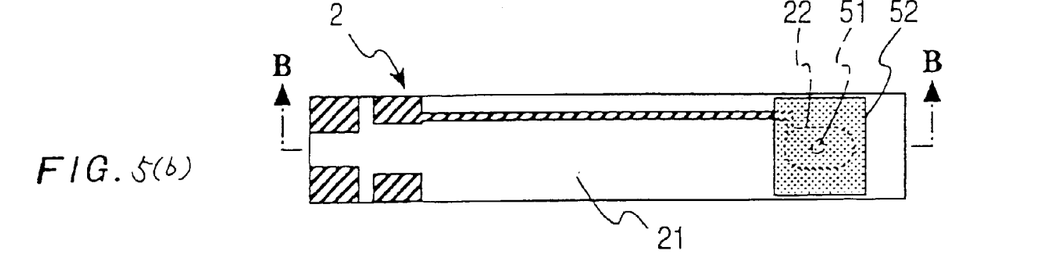
FIG. 5(b) is a plan view which shows a sensor element of the hydrogen sensor shown in FIG. 5(a)
Figure 5C:
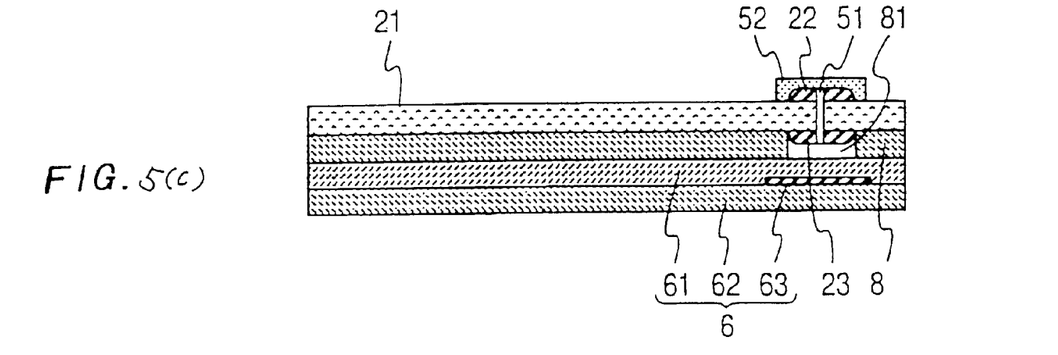
FIG. 5(c) is a cross sectional view taken along the line B—B in FIG. 5(b)

FIGS. 5(*a*), 5(*b*), and 5(*c*) show the hydrogen sensor 100 according to the third embodiment of the invention which is different from the second embodiment in that a protective layer 52 is disposed on the base 21 to cover the pin hole 51. Other arrangements are identical, and explanation thereof in detail will be omitted here.

The protective layer 52 is made of a porous material such as a porous alumina whose porosity is 3 to 30% and has a thickness of 10 to 200 μm. The use of the porous protective layer 52 causes the difference in speed of diffusion between hydrogen and oxygen contained in the gas when entering the chamber 81 to be increased, which results in an increase in change of the sensor output, as indicated by the middle solid line in FIG. 6, as compared with the second embodiment.

Figure 7:
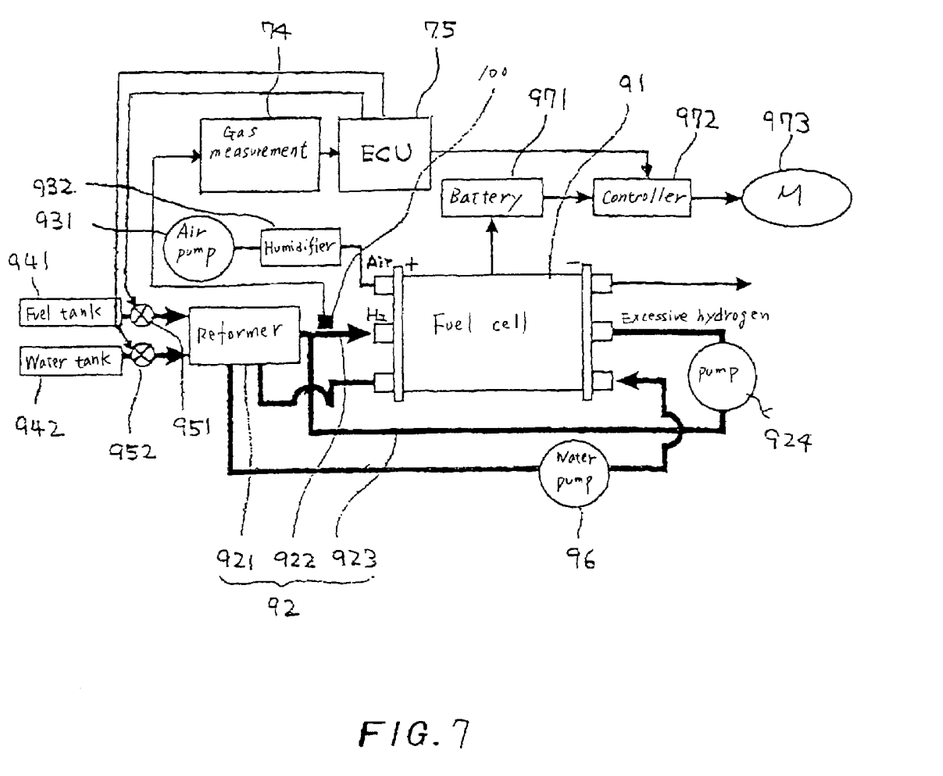
FIG. 7 is a block diagram which shows a hydrogen leakage detector mounted in a hybrid vehicle or an electric vehicle to detect a leakage of hydrogen from a fuel cell using a hydrogen sensor.

FIG. 7 shows a hydrogen leakage detector mounted in a hybrid vehicle or an electric vehicle to detect a leakage of hydrogen from a fuel cell.

The hydrogen leakage detector includes the hydrogen sensor 100 having one of the structures, as described above. The fuel cell 91 is connected to a hydrogen supply system 92. The hydrogen supply system 92 includes a reformer 921, a supply line 922, and a return line 923. The reformer 921 produces hydrogen using fuel such as methane supplied from a fuel tank 941 and water supplied from a water tank 942 and supplies it to a fuel electrode of the fuel cell 91 through the supply line 922. An air pump 931 is connected to a humidifier 932 and supplies air to an air electrode of the fuel cell 91. Specifically, the fuel cell 91 is supplied with the fuel and air to charge a battery 971. The fuel cell 91 is cooled by the water supplied by a water pump 96.

An excess of the hydrogen not consumed by the fuel electrode of the fuel cell 91 is discharged to the return line 923 and returned by a circulating pump 924 to the supply line 922.

The battery 971 provides a drive current to an electric motor 973 working as a power source of the vehicle through a controller 972 designed to perform, for example, PWM control.

The hydrogen sensor 100 is disposed near the supply line 922 of the hydrogen supply system 92 to measure the concentration of hydrogen leaking from the supply line 922. A gas measurement circuit 74 receives an output of the hydrogen sensor 100 and determines the concentration of hydrogen existing near the supply line 922 to provide a signal indicative thereof to an electronic control unit (ECU) 75.

The ECU 75 outputs a command signal to the controller 972 to have the motor 973 produce a given torque and controls switching operations of a fuel valve 951 and a water valve 952 based on the concentration of hydrogen near the supply line 922 determined by the gas measurement circuit 74. Specifically, when the concentration of hydrogen detected by the hydrogen sensor 100 exceeds a given value, the ECU 75 closes the fuel valve 951 and the water valve 952 to cut the supply of the fuel and water to the reformer 921 for avoiding an undesirable increase in leakage of hydrogen from the hydrogen supply system 92 to prevent the concentration of hydrogen existing around the hydrogen supply system 92 from exceeding an explosion limit.

The hydrogen sensor 100 may alternatively be installed near the reformer 921 or the return line 923.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

What is claimed is:

1. A method of measuring the concentration of hydrogen contained in a measurement gas which is substantially constant in a concentration of oxygen, comprising:
   using a limiting current oxygen sensor including a first and a second electrode formed on surfaces of a base of an oxygen ion-conductive solid electrolyte body and a diffusion resistor member working to restrict velocity of supply of the measurement gas to the first electrode;
   utilizing the diffusion resistor member which causes hydrogen to pass through the diffusion resistor member faster than oxygen in order to enhance sensitivity of measurement of the hydrogen; and
   applying voltage across the first and second electrodes to cause a limiting current to flow, as a sensor output between the first and second electrodes as a function of concentration of the oxygen in the measurement gas,
   wherein the concentration of hydrogen is measured based on a decrease in the sensor output caused by a decrease in concentration of the oxygen arising from reaction with the hydrogen.

2. The method as set forth in claim 1, wherein said diffusion resistor member comprises one of the group consisting of: a porous film and a film having a pin hole formed therein.

3. The method as set forth in claim 1, wherein said base has a test tube-like shape, and wherein the electrodes are disposed on opposed surfaces of said base.

4. The method as set forth in claim 1, wherein said base has a plate-like shape, and wherein the electrodes are disposed on opposed surfaces of said base.

5. The method as set forth in claim 4, wherein said base is formed by a laminate of plate members which forms a gas chamber therein, into which the measurement gas is introduced, one of the first and second electrodes being exposed to the gas chamber.

6. The method as set forth in claim 5, wherein a pin hole is formed in the laminate to establish communication between the gas chamber and an outside of a sensor element.

7. The method a set forth in claim 6, wherein a porous protective layer is formed on an outer surface of the laminate to cover the pin hole.

8. A method of detecting overcharge/overdischarge of a battery by measuring generation of hydrogen within a chamber of the battery during charge or discharge of the battery using the method as set forth in claim 1.

9. A method of detecting a hydrogen leakage from a hydrogen supply system using a method as set forth in claim 1 at a location near the hydrogen supply system which supplies hydrogen to a fuel cell.

* * * * *